United States Patent [19]

Pecenka

[11] Patent Number: 4,517,979

[45] Date of Patent: May 21, 1985

[54] DETACHABLE BALLOON CATHETER

[75] Inventor: Frank Pecenka, Miami Beach, Fla.

[73] Assignee: Cordis Corporation, Miami, Fla.

[21] Appl. No.: 513,697

[22] Filed: Jul. 14, 1983

[51] Int. Cl.³ ............................................ A61M 25/00
[52] U.S. Cl. ..................................... 128/325; 604/96;
604/99; 128/344
[58] Field of Search ............ 128/1 D, 325, 344, 348.1;
604/96–103

[56] References Cited

U.S. PATENT DOCUMENTS

| | | | |
|---|---|---|---|
| 3,834,394 | 10/1974 | Hunter et al. | 128/325 |
| 3,919,724 | 11/1975 | Sanders et al. | 3/36 |
| 4,029,104 | 6/1977 | Kerber | 128/348 |
| 4,085,757 | 4/1978 | Pesvner | 128/325 |
| 4,137,906 | 2/1979 | Akiyama et al. | 128/325 X |
| 4,282,875 | 8/1981 | Serbinenko et al. | 128/325 |
| 4,341,218 | 7/1982 | U | 128/325 |
| 4,364,392 | 12/1982 | Strother et al. | 128/325 |
| 4,395,806 | 8/1983 | Wonder et al. | 128/325 X |

FOREIGN PATENT DOCUMENTS 2019219 10/1979 United Kingdom.
542523 1/1977 U.S.S.R. .............................. 335/128

Primary Examiner—Dalton L. Truluck
Assistant Examiner—Christa K. Scott
Attorney, Agent, or Firm—Henry W. Collins; Thomas R. Vigil

[57] ABSTRACT

A detachable balloon catheter comprising a sealing valve assembly having an elongated passageway extending therethrough, an inflatable balloon having a mouth portion which is bonded to the periphery of the sealing valve assembly, and a small diameter cannula having a distal end which extends through the passageway in the sealing valve assembly. The small diameter cannula includes a connector terminal on the proximal end which is adapted to be coupled to a source of fluid pressure. The sealing valve assembly includes a valve mechanism which permits the passage of the cannula through the passageway but prevents the flow of fluid through the passageway when the cannula is removed. The balloon catheter also includes a cannula retainer mechanism which is formed of a resilient material and has an annular cavity for frictionally engaging the outer surface of the distal end of the cannula so that a predetermined force is required to withdraw the cannula from the retainer mechanism. The retainer mechanism is affixed to the inside surface of the balloon at a position diametrically opposite to the mouth of the balloon so that when the balloon is inflated to a desired size, the cannula is withdrawn from the retainer mechanism to thereby cause the balloon to become detached from the cannula.

6 Claims, 6 Drawing Figures

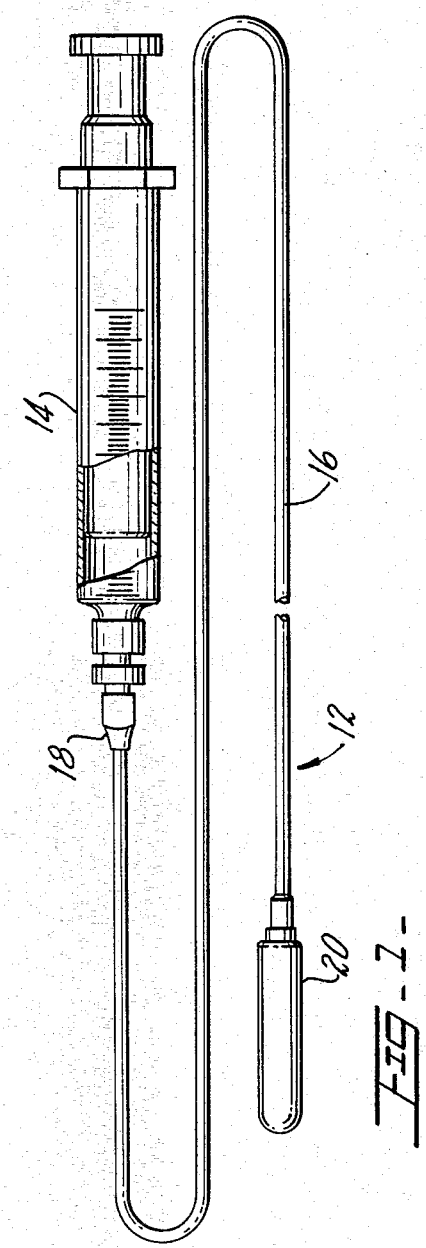
FIG. 1
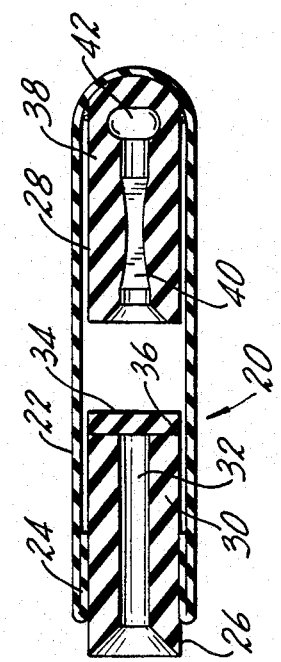
FIG. 2
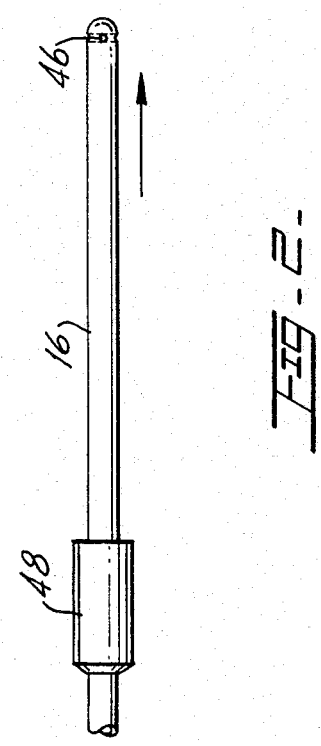

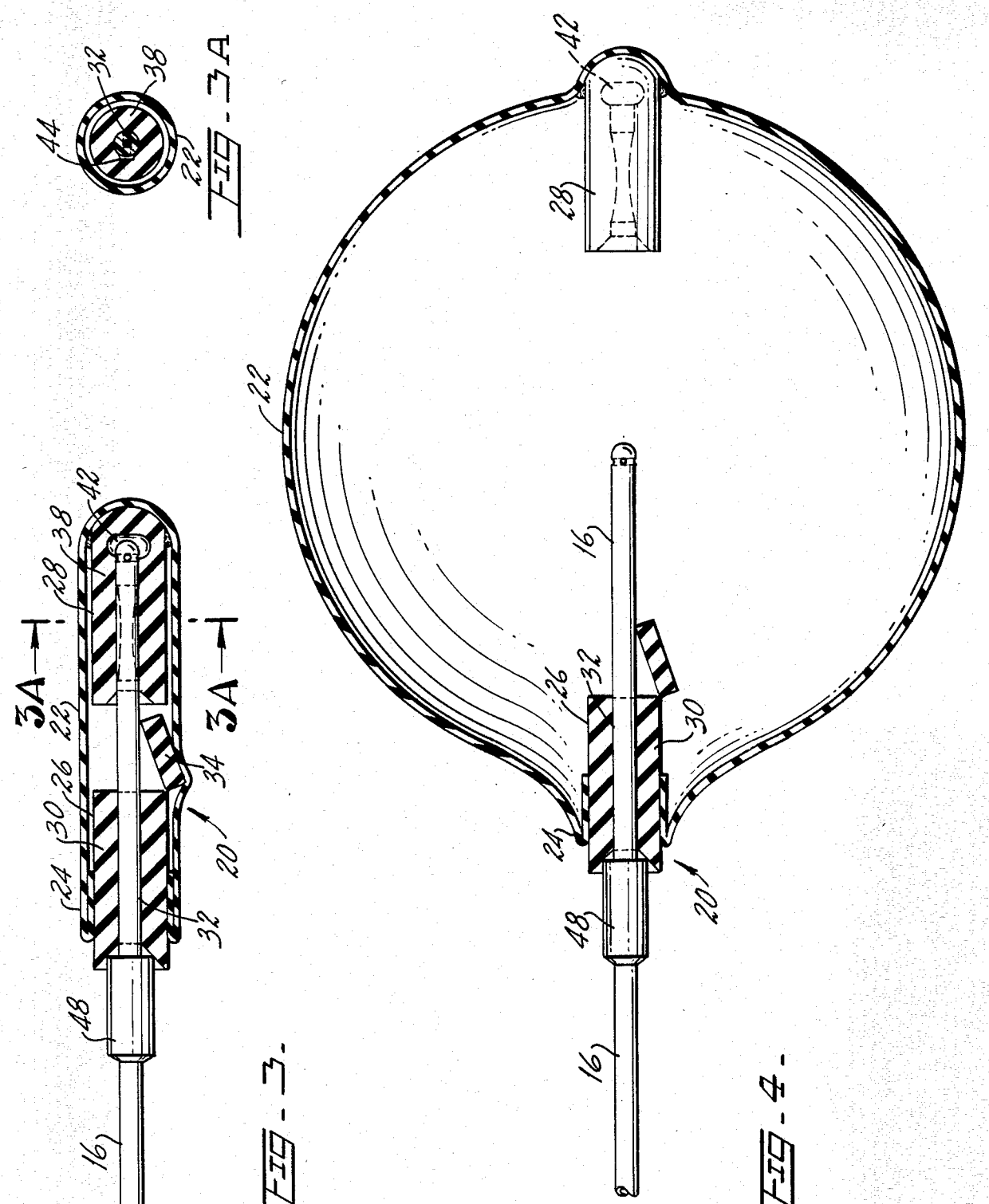

DETACHABLE BALLOON CATHETER

BACKGROUND OF THE INVENTION

This invention relates to the field of balloon catheters, and more particularly, to the field of miniaturized detachable balloon catheters for use in human blood vessels.

It has become a rather routine procedure to use balloon catheters to occlude vessels in certain types of cardiovascular surgery. In this procedure, an inflatable balloon which is positioned on the distal end of a cannula is inserted into a blood vessel and is either manually directed to a desired position in a blood vessel or is allowed to move to a desired position by circulation of blood through the vessel. When the balloon is properly positioned, it is then inflated by a fluid, or by a solidifying filler material, until the sides of the balloon are in contact with the walls of the blood vessel. The cannula may then be detached and withdrawn from the balloon, and the balloon may be left in the blood vessel in order to occlude the blood vessel.

One problem with such prior art detachable balloon catheters is that it is very difficult to precisely control the force required to withdraw the cannula from the balloon. As may be appreciated, if this force is too great, the balloon may be dislodged or repositioned in the blood vessel during detachment of the cannula. If the force required to withdraw the cannula from the balloon is too small, the balloon may become prematurely detached from the cannula during positioning of the balloon within the blood vessel.

Still another problem with such prior balloon catheters is that if a non-solidifying filler material, such as saline solution, is utilized to inflate the balloon, leakage of this material often occurs through the seal of the mouth of the balloon when the cannula is withdrawn from the balloon.

Accordingly, an important objective of the present invention is to provide a miniaturized detachable balloon catheter which may be used for permanent occlusion of a blood vessel, but one in which a cannula retainer mechanism automatically detaches the cannula from the balloon upon inflation of the balloon thereby preventing premature detachment of the balloon from the catheter.

Another objective of the present invention is to provide a miniaturized balloon catheter and a method of using the balloon catheter which is efficient in operation and relatively easy and inexpensive to manufacture.

SUMMARY OF THE INVENTION

According to one aspect of the present invention, a miniaturized detachable balloon catheter is inserted into a blood vessel and the balloon is inflated until the sides of the balloon are in contact with the walls of the vessel. Thereafter, the cannula which carries the balloon is withdrawn from the balloon and the balloon is sealed to prevent deflation of the balloon. More particularly, the mechanism for retaining the cannula to the balloon releases the cannula when the balloon has reached a desired size in order to cause the cannula to become detached from the inflated balloon. When the cannula is withdrawn from the balloon, a sealing valve closes thereby preventing delfation of the balloon.

The sealing valve includes a valve mechanism which permits the passage of the cannula through the passageway but prevents the flow of fluid through the passageway when the cannula is withdrawn from the balloon. The catheter retainer mechanism is formed of a resilient material and has an annular cavity for frictionally engaging the outer surface of the distal end of the catheter so that a predetermined force is required to withdraw the cannula from the retainer mechanism. The retainer mechanism is affixed to the inside surface of the balloon at a position diametrically opposite to the sealing valve so that when the balloon is inflated to a desired size, the catheter is automatically withdrawn from the retainer mechanism to thereby cause the balloon to become detached from the catheter.

To summarize, in general, the method and device of this invention deal with a miniaturized detachable balloon catheter assembly adapted for use in diagnostic and in therapeutic procedures in connection with human blood vessels. The device includes a cannula having a small outer diameter for insertion into such blood vessels. An inflatable balloon is mounted on the distal end of the cannula prior to insertion into the vessel. Upon insertion of the balloon into the vessel, the balloon is carried by the flow of blood through the vessel to a desired location. A fluid pressure is then applied to the proximal end of the cannula to inflate the balloon. The balloon catheter includes a mechanism for automatically detaching the balloon from the catheter upon inflation of the balloon.

BRIEF DESCRIPTION OF THE DRAWINGS

The foregoing and other objects, features and advantages of the invention will become apparent from the following description of a preferred embodiment of the invention, as illustrated in the accompanying drawings in which reference characters refer to the same parts throughout the different views. The drawings are not necessarily to scale, emphasis instead being placed upon illustrating the principles of the invention in a clear manner.

FIG. 1 is a plan view of a miniaturized detachable balloon catheter assembly illustrating a preferred embodiment of the present invention;

FIG. 2 is a sectional view which illustrates in more detail the balloon assembly prior to insertion of the catheter;

FIG. 3 is a sectional view of the balloon assembly illustrated in FIG. 2 with the catheter inserted but with the balloon shown in an inflated configuration;

FIG. 3a is a sectional view taken along line 3A-3A of FIG. 3 which illustrates in more detail the retainer mechanism of the balloon assembly;

FIG. 4 is a sectional view of the balloon assembly illustrated in FIG. 3 with the balloon fully inflated; and, FIG. 5 is a sectional view of balloon assembly illustrated in FIG. 4 with the cannula withdrawn from the balloon assembly.

DESCRIPTION OF THE PREFERRED EMBODIMENT

Figure 5:
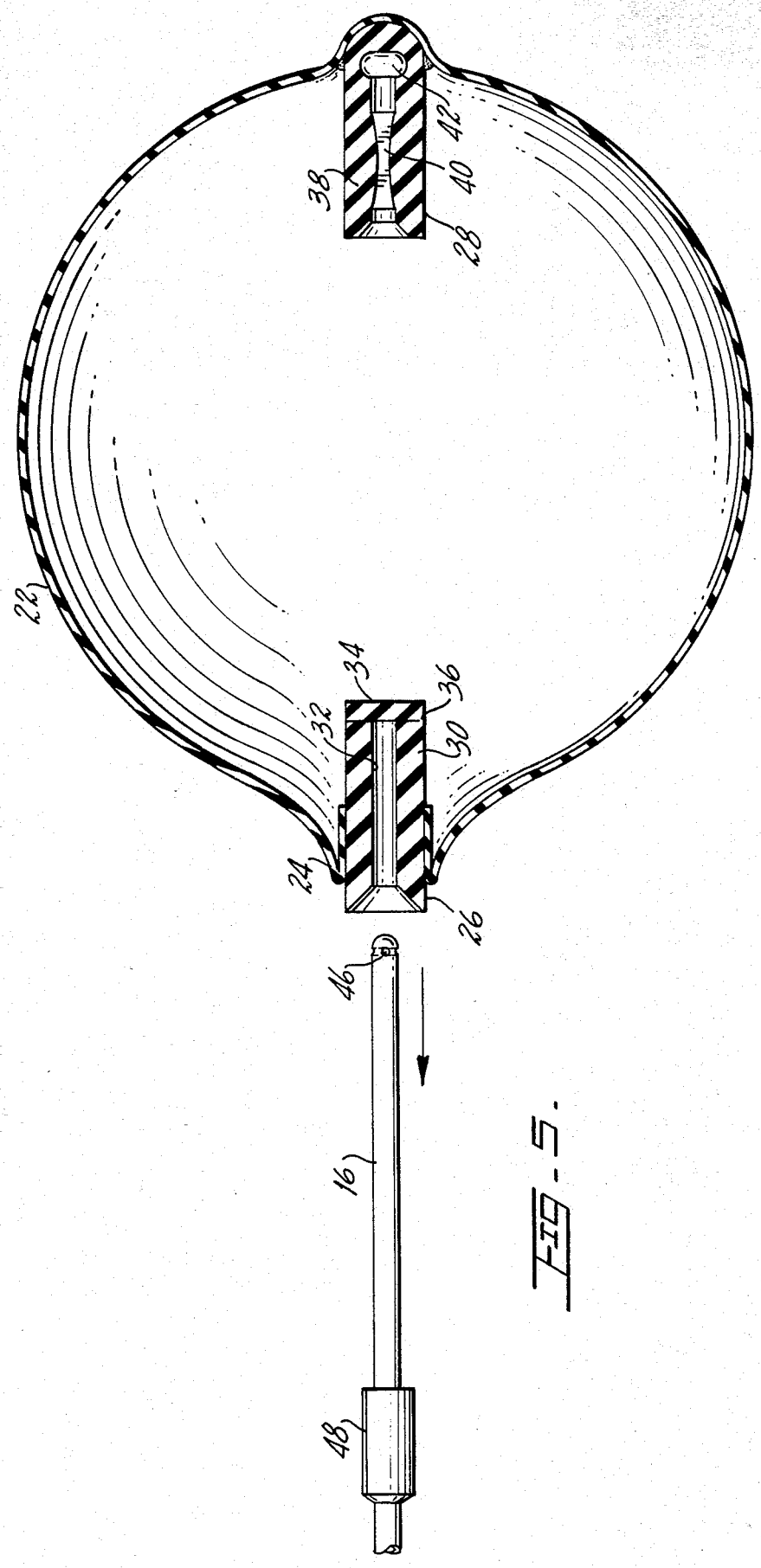

FIG. 1 generally illustrates a detachable balloon catheter assembly 12 which is a connected to a conventional source of pressurized fluid, such as a hypodermic syringe 14. The balloon catheter assembly 12 is comprised of an elongated cannula 16, having a connector 18 disposed on its proximal end for coupling the cannula 16 to the hypodermic syringe 14, in a balloon assembly 20 disposed on its distal end.

As illustrated in FIG. 2, the balloon assembly includes an inflatable balloon 22 having a mouth portion 24 which is bonded about the periphery of a sealing valve assembly 26. The balloon assembly 20 also includes a catheter retainer mechanism 28 which is affixed to the inside wall of the inflatable balloon 22 at a position diametrically opposite to that of the mouth 24 of the balloon 22.

More particularly, the balloon 22 is preferably fabricated from either latex or silicone rubber. The sealing valve assembly 26 generally takes the form of an elongated cylindrical sleeve 30 having a passageway 32 extending therethrough and a leaf or flap valve 34 positioned at one end of the cylindrical sleeve 30. The flap valve 34 is preferably formed integral with the cylindrical sleeve 30 and is formed by severing an end wall from the cylindrical sleeve 30 except to a small area which serves as a hinge 36. The sealing valve assembly is preferably fabricated from a material such as a suitable silicone composition such that when the flap valve 34 is formed by partially severing the end wall, the hinge 36 serves to cause the flap valve 34 to remain in a normally closed position as shown in FIG. 2. The passageway 32 is of a diameter substantially equal to the outside diameter of the distal end of the cannula 16 so that when the cannula 16 is inserted into the passageway 32 a generally fluid tight seal is established about the outside surface of the cannula 16.

As is illustrated, the mouth 24 of the inflatable balloon 22 is bonded about the periphery of the cylindrical sleeve 30 of the sealing valve assembly 26 in a manner so that the flap valve 34 is actually positioned within the inflatable balloon 22.

As also illustrated in FIG. 2, the catheter retainer mechanism 28 generally takes the form of a solid cylindrical body member 38 having a generally cylindrical cavity 40 which extends inwardly from an end wall of the cylindrical body member 38. The walls of the cylindrical cavity 40 are formed in a slightly convex configuration to form an inside diameter slightly less than the outside diameter of the cannula 16. The catheter retainer mechanism 28 is fabricated from a resilient material, such as a silicone composition, and the inside diameter of the convex portions of the sidewalls of the cavity 40 are of an inside diameter to frictionally engage the cannula 16.

The cylindrical cavity 40 is formed with an enlarged bulbous area 42 at the inside portion of the cavity 40 and as illustrated in FIGS. 3a, a slot extends along the sidewall over the entire length of the cylindrical cavity 40 in order to allow fluid which is applied into the bulbous area 42 of the cavity 40 to pass through the slot 44 and into the balloon 22.

The cannula 16 is of a generally conventional design with an aperture 46 extending through the wall of the catheter at the distal end thereof. The cannula 16 also includes a cylindrical sleeve 48 positioned about the outer surface of the cannula 16 at a predetermined distance from the distal end of the cannula 16. The cylindrical sleeve 48 serves to prevent the catheter from being inserted beyond a given distance through the sealing valve assembly 26 and, as will be discussed in more detail, the cylindrical sleeve 48 functions to assist in the removal of the cannula 16 from the retainer mechanism 28 upon inflation of the balloon 22.

FIG. 3 illustrates the balloon assembly 20 with the catheter 16 inserted through the sealing valve assembly 26 and into the retainer mechanism 28. In this configuration, the hinge 36 is shown in an open position, the cylindrical sleeve 30 provides a fluid-tight seal about the outside surface of the cannula 16, and the distal end of the cannula 16 is retained by the resilient sidewalls of the cylindrical cavity 40.

As illustrated in FIGS. 3 and 4, as a fluid is applied through the cannula 16, out of the apertures 46, through the slot 44 and into the inflatable balloon 22, the balloon begins to inflate. When the balloon 22 attains a certain volume of inflation, the balloon causes the retainer mechanism 28 to be moved to the right as illustrated in FIG. 4 thereby automatically withdrawing the distal end of the cannula 16 from the retainer mechanism 28. Once the cannula 16 is withdrawn from the retainer mechanism 28, as shown in FIG. 4, the cannula 16 may then be withdrawn from the sealing valve assembly 26 and the normally closed flap valve 34 closes thereby preventing fluid from leaking out of the inflated balloon 22.

Accordingly, with the detachable balloon catheter assembly of the present invention, the balloon remains attached to the cannula until the balloon is placed in a proper location within a blood vessel. Once the balloon is inflated beyond a given point, the cannula is automatically withdrawn from the retainer mechanism 28 and is then simply withdrawn through the sealing valve assembly 26 for subsequent removal from the vessel. The inflated balloon then serves to occlude the vessel at the desired position.

Having thus described my invention, it would become obvious that various materials may be used and modifications may be made, such as the utilization of various other forms of valves other than a flap valve, without departing from the spirit and scope of my invention. Accordingly, the invention should not be limited to the previously described preferred embodiment but should only be limited by the scope of the appended claims.

I claim:

1. A detachable balloon catheter assembly for use in human vessels comprising:

a small diameter cylindrical cannula having a distal end and a proximal end having connector terminal means on the proximal end for coupling the cannula to a source of fluid pressure;

a sealing valve assembly including a body member having a cylindrical passageway extending therethrough adapted to receive the distal end of said cannula thereby to provide a fluid tight seal against the outer surface of said cannula, said sealing valve assembly also including a valve means operative to permit the passage of said cannula through said valve assembly but preventing the flow of fluid through said valve assembly when said cannula is withdrawn from said valve assembly;

an inflatable balloon including a mouth portion at one end thereof, said mouth portion of the balloon being disposed about said sealing valve assembly;

retainer means including a body portion formed of a resilient material having a cylindrical cavity extending into said body portion, said cylindrical cavity of said retainer mean normally being of a diameter smaller than the outside diameter of said cannula so as to frictionally engage the outer surface of said cannula when said cannula is inserted into said cavity of said retainer means so that a predetermind force is required to withdraw said cannula from said retainer means, and said retainer means being affixed to the inside surface of said balloon at a position diametrically opposite to the mouth of the balloon said retainer means having means for permitting pressurized fluid supplied to the distal end of said cannula, when it is positioned at the inner end of said cavity, to escape from said retainer means into said balloon and when said balloon becomes inflated the distal end of the cannula can be withdrawn from said retainer means and said valve assembly thereby to cause the balloon to become detached from the cannula.

2. A detachable balloon catheter as defined in claim 1 wherein said cavity in said retainer means takes the form of an elongated cylindrical cavity which extends through an end wall of said retainer means and terminates within said retainer means; and said elongated cavity includes a longitudinal slot extending along a side wall of said cavity to facilitate escape of pressurized fluid from said distal end of said cannula at the inner end of said cavity.

3. A detachable balloon catheter as defined in claim 2 wherein said longitudinal slot extends along substantially the entire length of the retainer means.

4. A balloon catheter assembly comprising;
  a cannula having a distal end, and a proximal end adapted to be connected to a source of pressurized fluid;
  a valve assembly means having a passageway therethough, said passageway having a proximal end for receiving said cannula and a distal end throughwhich said cannula can extend;
  said valve assembly means having valve means at the distal end of said passageway for permitting passage of said cannula through aid valve assembly means and for closing said distal end of said passageway when said cannula is not present therein;
  an elastic balloon having a mouth fixed to and around said valve assembly means; and
  a retainer member fixed to the inner surface of said balloon opposite said mouth of said balloon and having a cavity means therein for receiving said distal end of said cannula and having means for permitting the escape of pressurized fluid from said cavity when said distal end of said cannula is received therein.

5. The balloon catheter assembly of claim 4 wherein said cavity is means is of smaller diameter to provide a snug fit around said distal end of said cannula.

6. The balloon catheter assembly of claim 4 wherein said cavity means is an elongate cylindrical cavity and said retainer member has an elongate slot opening onto said cavity and extending substantially the length thereof for facilitating the escape of pressurized fluid from said cavity into said balloon.

* * * * *